United States Patent [19]

Leunig et al.

[11] Patent Number: 4,524,614
[45] Date of Patent: Jun. 25, 1985

[54] TENNIS BALL EVALUATOR

[75] Inventors: Carl V. Leunig, Glenmont, N.Y.; Michael F. Susi, Windsor, Conn.

[73] Assignee: Tex-Tech Industries, Middletown, Conn.

[21] Appl. No.: 539,081

[22] Filed: Oct. 5, 1983

[51] Int. Cl.³ .............................................. G01M 9/00
[52] U.S. Cl. ...................................... 73/147; 73/105; 73/432 R
[58] Field of Search ........................ 73/13, 9, 104, 105, 73/147, 167, 862.38, 862.54, 432 R, 432 V, 432 Z, 432 SD

[56] References Cited

U.S. PATENT DOCUMENTS 2,700,305  1/1955  Kendall ................................. 73/147
3,714,824  2/1973  Bush ................................. 73/147 X

FOREIGN PATENT DOCUMENTS 489931  8/1938  United Kingdom .................. 73/147

Primary Examiner—Charles A. Ruehl
Attorney, Agent, or Firm—Kane, Dalsimer, Kane, Sullivan & Kurucz

[57] ABSTRACT

An apparatus and device for evaluating the surface roughness of a tennis ball or other objects. The object is placed in flowing gas and the drag force applied on the object is measured. By repeating the procedure with objects having different surface roughness a cross-reference table is developed between drag force and surface roughness. The apparatus comprises a scale supporting the object. The object is placed in a tube and gas is blown through the tube past the object, while the drag force on the object is measured by the scale.

7 Claims, 4 Drawing Figures

TENNIS BALL EVALUATOR

BACKGROUND OF THE INVENTION

1. Field of Invention

This invention pertains to a method and device for evaluating the performance of a ball in flight, and more particularly for evaluating the effects of wear and tear on the air resistance of the ball.

2. Description of the Prior Art

The resurgence of interest in the country in physical activities such as tennis and similar sports have led to improved sporting goods which last longer and perform better. Similarly a need developed for auxiliary equipment for monitoring the performance of the sporting equipment. For example in certain sports balls are projected through the air at high speed. The behavior of these balls is very much dependent on their surface characteristics and as the wear and tear associated with normal usage changes these surface characteristics, the behavior of the balls in flight changes also. This is especially true for tennis balls which initially have a $\frac{1}{8}$ to 3/16 inch surface nap. Because of this nap, tennis players are able to impart a spin on the ball which makes the ball change direction in mid-flight and bounce in unpredictable directions. However as the nap wears off it becomes harder to spin the ball. Therefore it is important for a tennis player to know the condition of different balls. Furthermore balls made by different manufacturers have different sized naps. The number and thickness of fibers per unit area also changes not only from one manufacturer to another but from one quality of ball to another even if made by the same manufacturer. Obviously both the density and the thickness of the fibers affect the characteristics of the ball. Yet until now the only way to determine these characteristics was by subjective visual inspection and comparison. However this was found to be unsatisfactory especially if the balls of different manufacturers are compared.

OBJECTIVES AND SUMMARY OF THE INVENTION

An objective of the present invention is to provide a method of determining the effects of usage on the characteristics of different tennis balls.

A further objective is to provide an apparatus for determining the flight characteristics of a ball.

Yet another objective is to provide an easy method and apparatus for determining the nap on a ball and its effects on the ball's aerodynamic behavior.

Further objectives and advantages shall become apparent in the detailed description of the invention.

The objectives are realized by placing a ball in the path of a stream of gas and measuring the drag force on the ball applied by said gas stream. A device for using this method comprises a tubular member, means of supporting a ball within said member, and means for determining the force of said gas stream on said ball as it flows past the ball.

DETAILED DESCRIPTION OF THE INVENTION

The principle of operation of the present device is based on the fact that the drag force caused by a fluid on an object while said object is surrounded by the fluid and the object and fluid are moving relative to each other depends on the corresponding Reynolds number, the relative velocity and the surface roughness of the object. Therefore if Reynolds number and the relative velocity are kept constant the surface roughness of the object may be quantitatively determined by measuring the drag force on the object. As the surface roughness of the object increases the drag force also increases.

Figure 1:
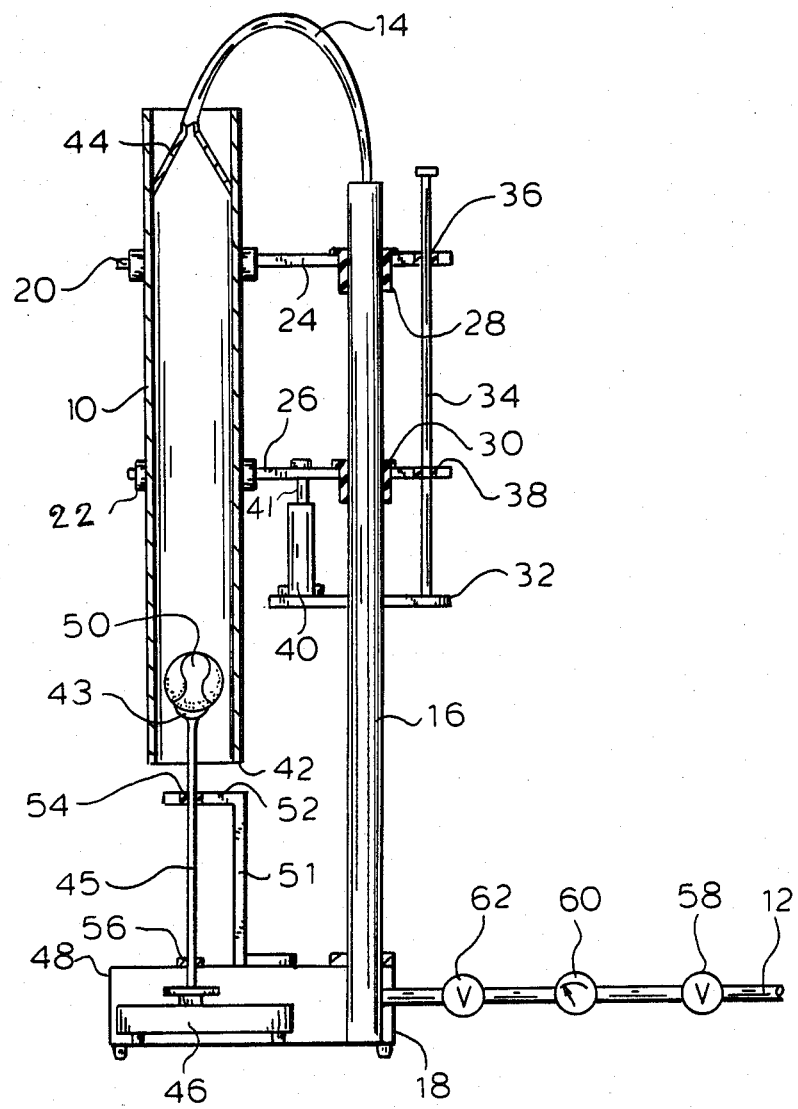
FIG. 1 shows a partial-cross-sectional elevation view of the preferred embodiment.

It would be very difficult to measure the forces of a tennis ball in flight. However since, as far as determining the drag force is concerned, it doesn't matter whether the fluid is moving with respect to the ball, in the present invention the ball is kept stationary and the air is blown or sucked past it. This is accomplished as shown in FIG. 1 by providing a tube 10 connected to a gas supply pipe 12 through flexible tubing 14, and a pipe 16. Pipe 16 is held in a substantially vertical position by a support housing 18 and is made of a rigid substance such as PVC or a metallic alloy so that it is strong enough to support tube 10.

Tube 10 is preferably made of a rigid material such as acrylic, PVC, or similar light plastic substance. Attached peripherally to the tube are two brackets 20 and 22. Each bracket is rigidly connected to a cross bar 24, 26. Cross bar 24 is rigidly attached to a bushing 28 which is slidably mounted on pipe 16. A similar bushing 30 is rigidly connected to cross bar 26.

Affixed to pipe 16 is a platform 32 which is supporting an anti-twist guide bar 34 which extends upward from the platform in parallel with pipe 16. Cross bars 24 and 26 are also rigidly connected to small bushings 36 and 38 respectively, said small bushings being slidably mounted on said guide bar. Thus tube 10 is movable in the vertical direction but its movement in any lateral direction is substantially eliminated by the guide bar. The bottom cross bar 26 is resting on a stop 40, which is also affixed to platform 32. Bracket 22, platform 32 and stop 40 are positioned so that when the cross bar 26 is resting on stop 40, the lower end 42 of tube 10 is at a predetermined height from base 18. In order to facilitate raising the tube, the tube may be equipped with a handle. Alternatively, stop 40 may comprise a cylinder with an air-activated piston 41 which, when air is supplied through a tubing (not shown) to the cylinder, pushes cross bar 26, and therefore tube 10 upward. Such assemblies are well known in the mechanical arts and therefore no further disclosure is necessary.

Preferably the upper end of tube 10 is closed and flexible tubing 14 is connected to said closed end through a funnel-shaped gas diffuser 44.

Under the lower end 42 of the tube is a rod 45 which extends substantially co-axially to tube 10. The lower end of rod 45 rests on a digital scale 46 while its upper end extends into the tube while the tube is in its rest position, and terminates in a cup 43. The cup is adapted to hold a tennis ball or any other ball 50 with a relatively rough surface. The diameter of the cup is smaller than the ball diameter so that the cup does not substantially interfere with the drag force measurements. Preferably the digital scale is of a kind which may be biased or tared to eliminate the effects of any weight resting on the scale at a given time. The scale preferably is disposed within the support housing 18 which has a protective top 48 right above the scale so that the gas flow from tube 10 does not affect it. A support frame 51 is attached to the top and extends upward terminating in a substantially horizontal member 52 with a hole 54. Within hole 54 there are anti-friction bearings so that the support frame 50 is adapted to support rod 45 which passes through hole 54 without interfering with its vertical movement. Rod 45 also passes through hole 56 made through top 48 so that it (the rod) rests on the scale.

The device operates as follows. Tube 10 is raised to allow the ball to be placed in cup 43 and then lowered back to the position shown in FIG. 1. In this position the ball is concentric to the tube and is placed far enough from the lower end 42 so that any eddy currents or other boundary phenomena generated at the lower end have no effect or a constant effect on the measurements. At this point the digital scale is biased or tared to read "0" to eliminate the weight of ball 50 and rod 45. A gas from supply pipe 12 passes through a pressure regulator 58, a flow or pressure gauge 60 and a needle valve 62, into pipe 16 through flexible tubing 14 and tube 10. The gas can be air or any other gaseous substance.

Once the gas reaches tube 10 it is diffused by diffuser 44 and it starts flowing in a substantially uniform manner through the tube. As the gas passes the ball, the ball experiences a drag force which, as explained above, is directly related to the ball's surface roughness. This force is measured and displayed by the digital scale.

By repeating the above procedure with several balls of the same type and make which have gone through different levels of usage and therefore having different surface roughness characteristics, a table may be quickly established to correlate the surface roughness of a ball to the drag force on the ball within tube 10. Similarly the surface roughness of different type and/or make of balls may be compared by merely comparing the respective drag forces. Of course in order for the measurements to be consistent the gas flow within tube 10 must be substantially identical each time a measurement is made. This is accomplished by adjusting the needle valve 62 before the measurements, until the desired gas flow, as indicated by flow or pressure gauge 60 is reached.

For best results a digital scale is preferable because such scales are known for their reliability and accuracy. However any other force measuring device may be substituted for the scale such as a force transducer, a strain gauge, a spring type scale, a balanced beam scale etc. The choice of the scale to be used with the invention depends on the actual use for the device. If the device is used as part of a new design program or quality assurance, the scale must be accurate to show minute surface roughness differences. On the other hand if the device is used at or near a tennis court or tennis shop, a less accurate scale may be used with a simple indication of only two or three zones to show that a given ball is "good", "marginal" or needs "replacement".

Figure 2:
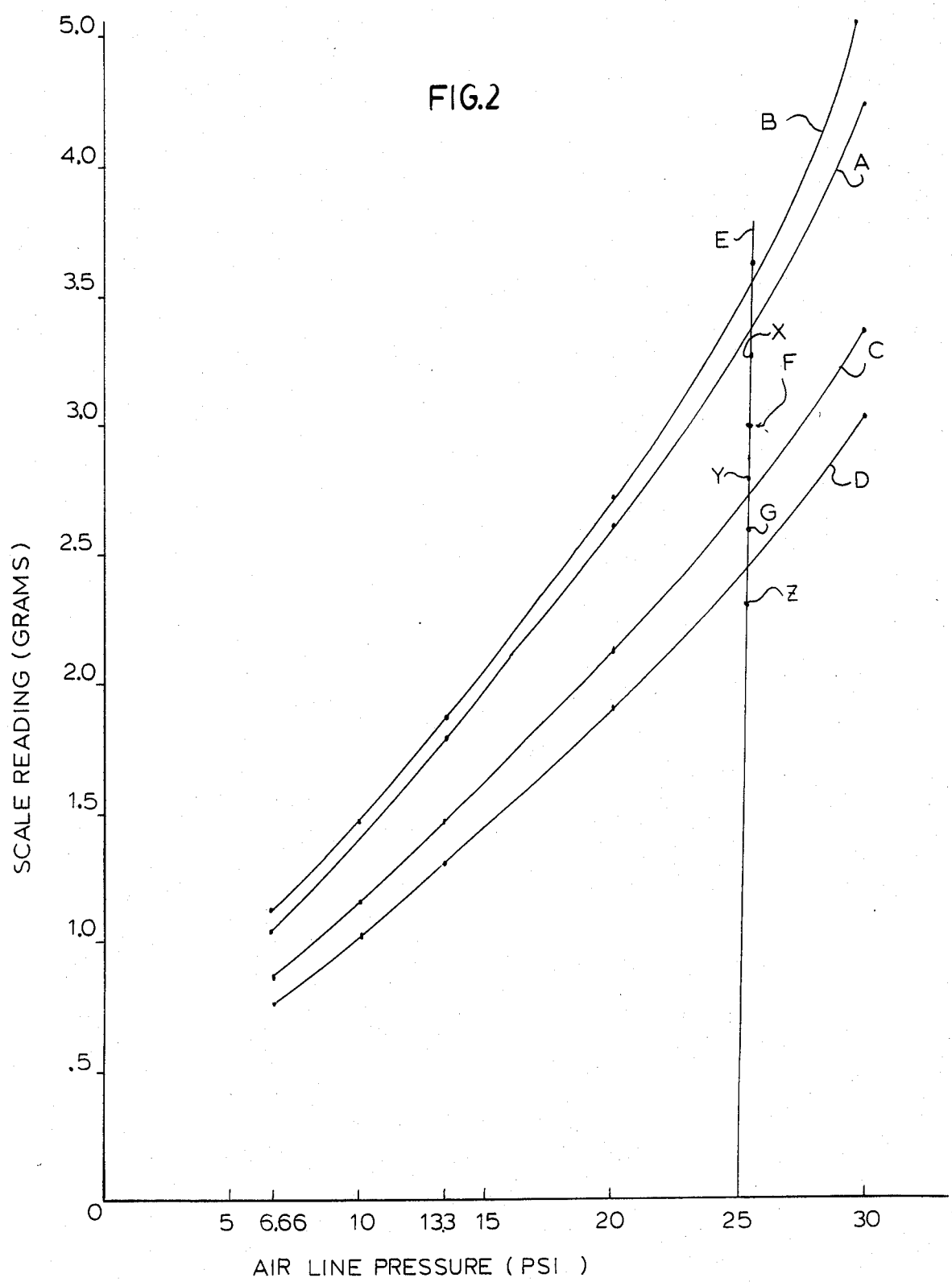
FIG. 2 shows the average response curves of the apparatus of FIG. 1.

The apparatus of FIG. 1 has been used by the inventor to study the effects of wear on the drag force. The results of the study are shown in FIG. 2 wherein the horizontal line represents the pressure of air supplied to tube 10 as measured by gauge 60, and the vertical line represents the tared reading of scale 46. The balls from four different groups A, B, C and D were each inserted in the device, and the scale readings were recorded as the pressure of the gas was varied from 5 to 30 psig. The readings from each groups were averaged and the four curves A–D, shown on FIG. 2 were obtained. Group A consisted of brand new balls. Group B consisted of slightly used balls. Group C and D consisted of moderately and heavily used balls respectively.

An analysis of FIG. 2 provides two important observations. First, curve B, shows that the drag on slightly used balls is consistently higher than the drag on brand new balls. At first impression this is surprising since one would expect that the drag would continuously decrease as the nap of the ball wears away. This anomaly is explained by the fact that while brand new balls are stored their nap is compacted so that they offer little resistance to air. After a ball has been used a couple of times, the collisions with rackets, and ground actually fluff up the ball's nap so that the ball presents more resistance to air as illustrated by curve B.

Figure 3:
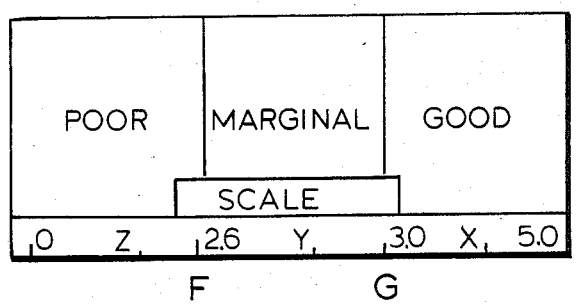
FIG. 3 shows a typical chart prepared for a player in accordance with the curves of FIG. 2.

Secondly, the separation between the curves increases drastically with pressure. Thus, while at 5 psig curves D and B are separated by only 0.35 g, at 30 psig this separation increases to 1.05 g. This indicates the device is most effective at higher pressures. For example if a pressure of 25 psig is chosen then all the readings taken with the subject device lie along line E of FIG. 2. If a point F is chosed to be approximately half way between curves A and C and point G is chosen half way between curves C and D, then the condition i.e. the aerodynamic properties of a ball are determined by taking a reading on the device and determining the position of the reading relative to points F and G on line E. For example if a reading corresponding to point X above point F is obtained for a particular ball, this indicates that the ball still has an acceptable nap. Similarly readings corresponding to points Y (lying between points F and G) and Z (lying below G) indicate respectively marginal and poor balls. To facilitate this determination a chart has been prepared as shown on FIG. 3 corresponding to line E. If the device is set to operate at 25 psig, a player can put his ball into a device, get a reading from the scale and look at the chart of FIG. 3 to determine the condition of the ball. Points X, Y, and Z on chart 3 correspond to the same points on FIG. 2. The legends above each zone indicate the respective condition of the ball corresponding to a reading.

The relatively large separation between the curves at 25 psig insures that various secondary effects do not affect the determination. Such secondary effects include slight variation of the ball diameters from a nominal value, localized or uneven wear of the ball and the positioning and relative area of the surface seams of the ball cover.

Figure 4:
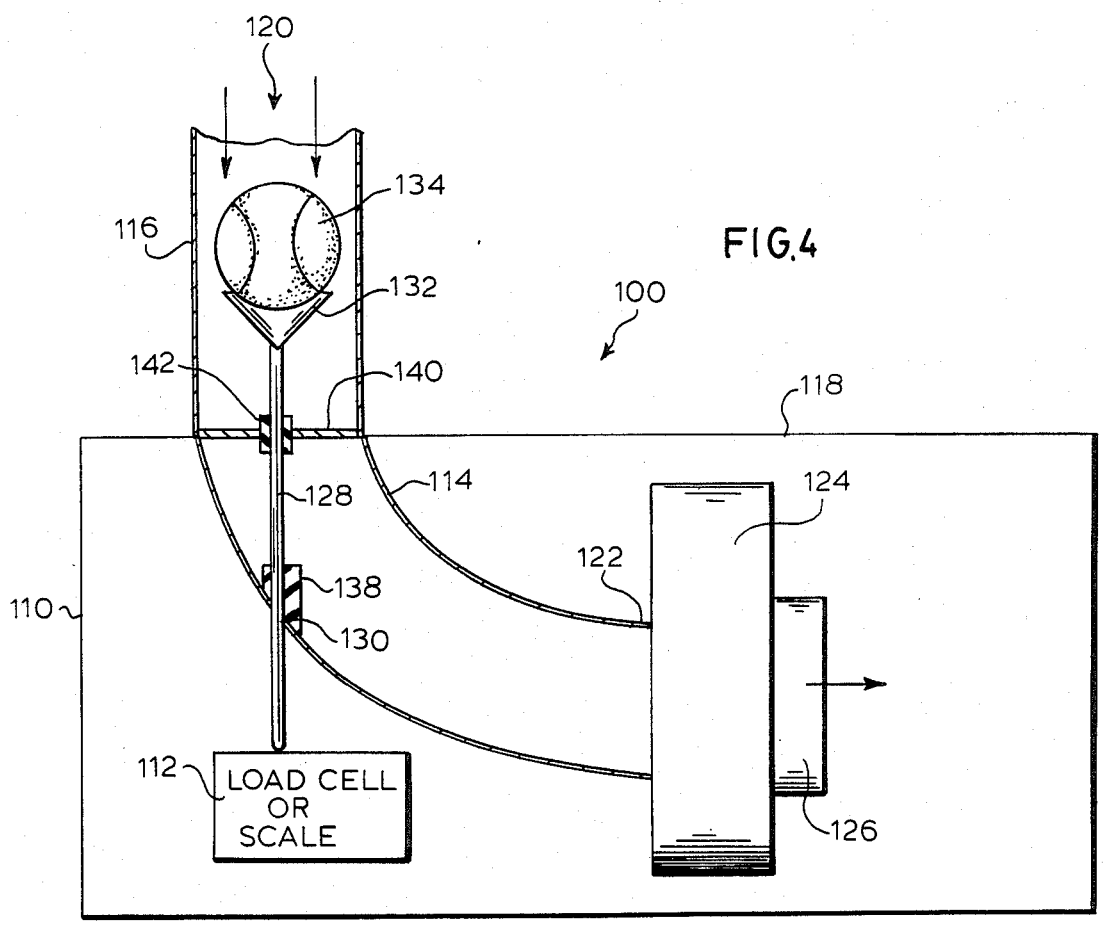
FIG. 4 shows an alternate embodiment.

An alternate embodiment of the invention is shown in FIG. 4. The principle of operation of this embodiment is identical to the principle for the device of FIG. 1. The main difference is that while in the first embodiment air is being pushed passed the ball in this second embodiment the air is sucked or pulled passed the ball.

The device 100 of FIG. 4 comprises an enclosure or housing 110. Inside the housing there is a scale 112 and an elbow-shaped pipe 114. The elbow has a substantially vertical mouth 116 extending above the top surface 118 of the enclosure which is opened as at 120. At its other end 122, the elbow is connected to a standard blower 124 provided to suck air from the outside of the enclosure through opening 120 of mouth 116 and pipe 114. The blower is provided with control vanes 126 which are used to control the rate of air flow through the pipe thereby controlling the speed of the air stream flowing therethrough.

A substantially vertical stem 128 extends from the scale 112 through opening 130 of the pipe and terminates in a cup 132. Scale 112, pipe 114 and stem 128 are positioned and arranged so that cup 132 is disposed within the mouth portion 116 of the pipe. The cup 132 is provided to hold ball 134. Preferably the cup is disposed coaxially within mouth 116. Furthermore, as shown in FIG. 4, opening 120 should be at least a couple of inches higher than the ball so that as the air enters the pipe boundary effects caused by the mouth are negligible by the time the air flows passed the ball 134.

A bushing 138 is provided through hole 130 to allow stem 128 to move vertically with respect to pipe 114 while minimizing the effect of friction. The bushing also acts as a sealing means so that air does not enter the pipe through hole 130.

In order to keep stem 128 vertical, a horizontal member 140 is provided with roller bearing 142. The member 140 is affixed to the sides of pipe 114 and permits stem 128 to move up and down without applying to it any substantial frictional forces. The stem, while being held vertically by the bushing 138 and bearing 142, rests on the scale 112. Thus, the scale registers the weight of the stem, the weight of the ball, and when the blower is activated, the drag force of the ball induced by the air flowing around it. Thus it is evident that this device functions in the manner of the device of FIG. 1. The readings of the scale are normalized by eliminating the weight of the ball and stem and by adjusting the vanes. Thus a plurality of such devices can be normalized by using the same balls and adjusting the vanes until the same reading is obtained on all the devices. This operation automatically compensates for inherent variations in the shape and layout of individual pipes.

Although the invention was described specifically for evaluating tennis balls, it is clear that the method and apparatus disclosed herein can be used to measure the surface characteristic of numerous other objects.

One skilled in the art may make numerous modifications of the preferred embodiment described above without departing from the scope of the invention as defined in the appended claims.

We claim:

1. A tennis ball evaluator comprising:
   a tube;
   means for supporting a tennis ball within said tube;
   means for causing a gas to flow through said tube to generate a drag force on said tennis ball; and
   a scale operatively connected to said supporting means for determining said drag force.

2. The tennis ball evaluator of claim 1 whereby said means for causing a gas to flow through said tube comprising a gas source and a pipe connected between said gas source and said tube.

3. The tennis ball evaluator of claim 2 wherein said means for supporting said tennis ball comprises a support frame disposed on and extending above said scale; and said tube is disposed above said scale and partially surrounds said support frame.

4. The evaluator of claim 3 further comprising a cover disposed between said scale and said tube to protect said scale.

5. The evaluator of claim 3 wherein said tube is movable with respect to said support frame to allow a tennis ball to be placed on and removed from said support frame.

6. The tennis ball evaluator of claim 1 wherein said means for causing gas to flow through said tube comprises a blower connected to one end of said tube and adapted to suck air out of said tube, the other end of the tube being open.

7. The tennis ball evaluator of claim 6 wherein said tube is in the shape of an elbow and said means for supporting said tennis ball extends through a side-wall of said tube.

* * * * *